US 12,383,671 B2

(12) United States Patent
Augustine et al.

(10) Patent No.: US 12,383,671 B2
(45) Date of Patent: *Aug. 12, 2025

(54) IV EXTRAVASATION DETECTION DEVICE

(71) Applicant: Augustine Biomedical and Design, LLC, Eden Prairie, MN (US)

(72) Inventors: Scott D. Augustine, Deephaven, MN (US); Randall C. Arnold, Minnetonka, MN (US); Garrett J. Augustine, Deephaven, MN (US)

(73) Assignee: Augustine Biomedical and Design, LLC, Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/630,860

(22) Filed: Apr. 9, 2024

(65) Prior Publication Data

US 2024/0342372 A1    Oct. 17, 2024

Related U.S. Application Data

(63) Continuation of application No. 16/781,609, filed on Feb. 4, 2020, now Pat. No. 11,957,873.

(51) Int. Cl.
*A61M 5/168* (2006.01)
*A61M 25/02* (2006.01)
*A61M 5/158* (2006.01)

(52) U.S. Cl.
CPC ........ *A61M 5/16836* (2013.01); *A61M 25/02* (2013.01); *A61M 2005/1588* (2013.01);
(Continued)

(58) Field of Classification Search
CPC .............. A61M 5/16836; A61M 25/02; A61M 2205/584; A61M 2205/15;
(Continued)

(56) References Cited

U.S. PATENT DOCUMENTS 3,618,602 A    11/1971  Shaw
4,633,863 A    1/1987   Filips et al.
(Continued)

FOREIGN PATENT DOCUMENTS

EP    2328648 B1    5/2016

OTHER PUBLICATIONS

International Patent Application No. PCT/US2016/063328, International Search Report and Written Opinion mailed Mar. 3, 2017, 18 pages.

(Continued)

*Primary Examiner* — Nathan R Price
*Assistant Examiner* — Anna E Goldberg-Richmeier
(74) *Attorney, Agent, or Firm* — Fredrikson & Byron, P.A.

(57) ABSTRACT

A fluid extravasation detection device detects the subcutaneous extravasation of fluid from a vein containing an intravenous (IV) catheter. The device includes one or more first temperature sensors for positioning on skin near an entry point of the IV catheter into the vein, and one or more second temperature sensors for positioning on skin near a tip of the subcutaneously located IV catheter. The first and second temperature sensors are operably connected to an electronic thermometer that compares the temperature difference between a first temperature and a second temperature. The first temperature is determined based on temperature detected by at least one of the one or more first temperature sensors. The second temperature is determined based on temperature detected by at least one of the one or more second temperature sensors. An alarm is activated if the difference between the first and second temperatures changes more than a predetermined amount.

25 Claims, 13 Drawing Sheets

(52) U.S. Cl.
CPC . *A61M 2025/0266* (2013.01); *A61M 2205/15* (2013.01); *A61M 2205/18* (2013.01); *A61M 2205/3368* (2013.01); *A61M 2205/581* (2013.01); *A61M 2205/584* (2013.01); *A61M 2205/587* (2013.01)

(58) Field of Classification Search
CPC ........ A61M 2205/587; A61M 2205/18; A61M 2205/3368; A61M 2205/581; A61M 2025/0266
See application file for complete search history.

(56) References Cited

U.S. PATENT DOCUMENTS

| | | | |
|---|---|---|---|
| 4,647,281 | A | 3/1987 | Carr |
| 5,334,141 | A | 8/1994 | Carr et al. |
| 5,827,707 | A | 10/1998 | Lamberti |
| 6,827,707 | B2 | 12/2004 | Wright et al. |
| 7,546,776 | B2 | 6/2009 | Ono |
| 10,507,153 | B2 | 12/2019 | Augustine et al. |
| 10,512,191 | B2 | 12/2019 | Augustine et al. |
| 2003/0036713 | A1 | 2/2003 | Bouton et al. |
| 2006/0135884 | A1 | 6/2006 | Bouton et al. |
| 2007/0016068 | A1 | 1/2007 | Grunwald et al. |
| 2009/0149814 | A1 | 6/2009 | Bailey et al. |
| 2009/0182283 | A1 | 7/2009 | Sloan |
| 2012/0197204 | A1 | 8/2012 | Helm, Jr. |
| 2013/0131506 | A1 | 5/2013 | Pollack |
| 2013/0237779 | A1 | 9/2013 | Warren et al. |
| 2013/0338511 | A1 | 12/2013 | Warren et al. |
| 2014/0074037 | A1 | 3/2014 | Bornhoft |
| 2015/0305629 | A1 | 10/2015 | Fritz et al. |
| 2017/0143941 | A1 | 5/2017 | Augustine et al. |
| 2017/0367654 | A1 | 12/2017 | Cheng et al. |
| 2020/0324045 | A1 | 10/2020 | Inoue et al. |
| 2023/0052494 | A1 | 2/2023 | Padmanathan et al. |

OTHER PUBLICATIONS

"Response to Restriction Requirement", From U.S. Appl. No. 18/630,817, filed Aug. 20, 2024, pp. 2.
United States Patent Office, "Office Action", From U.S. Appl. No. 18/630,817, Dated Sep. 5, 2024, pp. 12.
United States Patent Office, "Restriction Requirement", From U.S. Appl. No. 18/630,817, Dated Jun. 20, 2024, pp. 6.
"Amendment and Response to Office Action", From U.S. Appl. No. 18/630,817, filed Dec. 5, 2025, pp. 9.
United States Patent Office, "Final Office Action", From U.S. Appl. No. 18/630,817, Dated Jan. 2, 2025, pp. 12.
"Amendment and Responses to Office Action", From U.S. Appl. No. 18/630,817, Filed Jun. 2, 2025, pp. 9.
United States Patent Office, "Office Action", From U.S. Appl. No. 18/630,817, Filed Jun. 2, 2025, pp. 9.

IV EXTRAVASATION DETECTION DEVICE

RELATED APPLICATION

This application is a continuation of U.S. application Ser. No. 16/781,609, filed Feb. 4, 2020, the entire contents of which is incorporated herein by reference.

BACKGROUND OF THE INVENTION

It is very common for intravenous (IV) catheters to create a leakage of fluid and/or blood from the vein into which they are inserted, out to the surrounding subcutaneous tissue. This leakage is referred to as "fluid extravasation." In general, IV catheters cause extravasation in one of three ways. First, fluid can leak from the hole in the vein wall where the catheter has entered the vein. Second, the catheter can inadvertently be pulled out of the vein and yet the tip of the catheter remain in the subcutaneous tissue infusing directly into the subcutaneous tissue. In such a case, blood and fluids being administered through the catheter would be delivered into the subcutaneous tissue rather than into the intravenous space. Finally, the tip of the catheter can erode a hole in the vein wall and protrude through the hole infusing directly into the subcutaneous tissue.

When extravasation is occurring, the IV, which may be the lifeline for the patient, is not functioning properly. In fact, some (if not all) of the fluids and drugs being administered are not being delivered to the bloodstream where they can be effective. Rather, they are creating a swollen area in the soft tissue. If the IV fluid is simply a physiologic salt solution such as saline, the swelling may not be a serious problem and will likely resolve without lasting consequence. On the other hand, if the drugs being delivered are toxic (like many drugs, including chemotherapeutics), or are strong vasoconstrictors (like epinephrine, norepinephrine or phenylephrine), extravasation into the subcutaneous tissue can result in massive tissue necrosis and serious lasting injury to the patient. This scenario is much more common and severe in the pediatric patient population where smaller IVs tend to be much less secure and easier to dislodge than in adults.

Currently, there is no monitor that can detect IV extravasation and sound an alarm for the caregiver to inspect the patency of the IV. Frequent visual inspection by the caregiver is currently the only way to detect IV extravasation. Clearly there is a need for a reliable and inexpensive IV extravasation monitor.

SUMMARY OF THE INVENTION

The fluid extravasation detection device of this disclosure is intended for use in medical settings generally. These include the operating room, the emergency room, the intensive care unit, hospital rooms, nursing homes, and other medical treatment locations.

Fluid extravasation from IVs is known to occur primarily at two locations, which include the entry point of the catheter into the vein and at the tip of the catheter poking through an inadvertent hole in the vein caused by the tip. Therefore, the present fluid extravasation detection device places fluid detection sensors adjacent one or both of these two locations. In some embodiments, two or more thermometers are used as the fluid extravasation sensors.

In some examples, the fluid extravasation detection device of the present disclosure positions one or more skin temperature sensors, such as thermistors or thermocouples, on to the skin of a patient adjacent the entry point of the catheter into the vein to detect a first skin temperature of the patient. In such examples, one or more skin temperature sensors are also positioned on the skin adjacent the tip of the catheter to detect a second skin temperature of the patient. Since these two locations are separated by only 4-5 cm, it is expected that the first and second skin temperatures should be nearly identical under normal conditions. In some examples, the two or more skin temperature sensors (e.g., thermistors or thermocouples) advantageously may not need to be calibrated. Avoiding calibration saves costs but may result in the two skin temperature sensors indicating slightly different temperatures, even though the skin at these two locations are the same temperature. In this case, the starting delta or difference between the first and second skin temperatures would be the baseline temperature delta (baseline $\Delta T$). Since IV fluids are virtually never the same temperature as the arm that they are being infused into, any change in the baseline $\Delta T$ between the first and second skin temperatures most likely indicates fluid extravasation from the entry point of the catheter into the vein or from a hole in the vein caused by the catheter tip.

In some examples, the first and second skin temperature sensors are operably connected to an electronic thermometer that can compare the difference between the first and second skin temperatures over time. A change in the first skin temperature or second skin temperature, indicates that cold or warm fluids may be extravasating from either the entry point of the catheter into the vein or from a hole in the vein caused by the catheter tip. The extravasating cold or warm fluids cause the adjacent skin temperature sensor to be cooler or warmer than the skin temperature sensor adjacent the non-extravasating portion of the IV catheter. In some embodiments, if the temperature difference between the first and second skin temperatures changes over time by more than a predetermined threshold (0.2° C., for example), an alarm is activated.

In some examples, the two or more skin temperature sensors are attached to one or more anchoring platforms to aid in the stabilization, location and attachment of the skin temperature sensors to the skin. In some examples, one or more holes may perforate the anchoring platform(s) to serve as a mounting location for the two or more skin temperature sensors, allowing the skin temperature sensors to be in direct thermal contact with the skin below. The anchoring platform(s) are then adhesively attached to the skin adjacent the subcutaneously located IV catheter.

In some examples, the two or more skin temperature sensors are attached to an IV catheter anchoring device that serves the same purpose as the anchoring platforms. Some examples of IV catheter anchoring devices have been previously disclosed in U.S. patent application Ser. No. 14/950,502, the entire disclosure of which is incorporated herein by reference. In some examples, the IV catheter anchoring device includes a skin attachment portion that can be made of flat, molded plastic that can be adhesively attached to the skin adjacent the subcutaneously located IV catheter. Similar to the other anchoring platforms of this disclosure, the skin attachment portion of a catheter anchoring device may include two or more holes that serve as mounting locations for the two or more skin temperature sensors.

In some examples, using a catheter anchoring device to serve as the anchoring platform is advantageous because the location of the entry point of the catheter into the vein and the tip of the catheter is known relative to the IV anchoring device. Therefore, the preferred location of the two or more skin temperature sensors relative to the vein and catheter are predetermined locations on the catheter anchoring device.

The catheter anchoring device thus allows rapid and reliable placement of the skin temperature sensors in precise locations relative to both the entry point of the IV catheter into the vein and the location of the tip of the catheter that may have eroded out of the vein.

Certain embodiments provide a fluid extravasation detection device for detecting the subcutaneous extravasation of fluid from a vein containing an intravenous (IV) catheter. The device includes one or more first temperature sensors for positioning on skin near an entry point of the IV catheter into the vein, and one or more second temperature sensors for positioning on skin near a tip of the subcutaneously located IV catheter. The one or more first and one or more second temperature sensors are operably connected to an electronic thermometer configured to compare a temperature difference between a first temperature and a second temperature over time, wherein the first temperature is determined based on temperature detected by detected by at least one of the one or more first temperature sensors, and the second temperature is determined based on temperature detected by at least one of the one or more second temperature sensors. An alarm is configured to be activated if the temperature difference between the first temperature and the second temperature changes more than a predetermined amount over time.

Certain other embodiments provide a fluid extravasation detection device for detecting the subcutaneous extravasation of fluid from a vein containing an intravenous (IV) catheter. The device includes one or more first temperature sensors for positioning on skin near an entry point of the IV catheter into the vein, and one or more second temperature sensors for positioning on skin near a tip of the subcutaneously located IV catheter. The one or more first and one or more second temperature sensors are held in contact with the skin by a skin attachment portion of a catheter anchoring device. The catheter anchoring device includes a catheter capture portion and a skin attachment portion. The catheter capture portion is configured to engage with a portion of the catheter. The skin attachment portion is coupled to the catheter capture portion and is configured to adhesively attach the catheter anchoring device to the skin. The skin attachment portion comprises an adhesive surface configured to adhesively attach the catheter anchoring device to the skin. More than 50% of the adhesive surface of the skin attachment portion extends beyond the catheter capture portion in a direction along the elongation of the catheter, and is positioned on opposite sides along the elongation of the catheter. The one or more first and one or more second temperature sensors are operably connected to an electronic thermometer configured to compare the temperature difference between a first temperature and a second temperature over time, wherein the first temperature is determined based on temperature detected by at least one of the one or more first temperature sensors, and the second temperature is determined based on temperature detected by at least one of the one or more second temperature sensors. An alarm is configured to be activated if the temperature difference between the first and second temperatures changes more than a predetermined amount over time.

Certain other embodiments provide a method of detecting the subcutaneous extravasation of fluids from a vein containing an intravenous (IV) catheter. The method includes adhesively attaching one or more first temperature sensors to skin near an entry point of the IV catheter into the vein, and adhesively attaching one or more second temperature sensors to skin near a tip of the subcutaneously located IV catheter. The method further includes operably connecting the one or more first and one or more second temperature sensors to an electronic thermometer that is configured to compare temperature differences between a first temperature and a second temperature over time, wherein the first temperature is determined based on temperature detected by at least one of the one or more first temperature sensors, and the second temperature is determined based on temperature detected by at least one of the one or more second temperature sensors. The method further includes activating an alarm if the temperature difference between the first temperature and the second temperature changes more than a predetermined amount over time.

DETAILED DESCRIPTION OF PREFERRED EMBODIMENTS

The following detailed description is exemplary in nature and is not intended to limit the scope, applicability, or configuration of the invention in any way. Rather, the following description provides practical illustrations for implementing various exemplary embodiments. Examples of constructions, materials, dimensions, and manufacturing processes are provided for selected elements, and all other elements employ that which is known to those of skill in the field. Those skilled in the art will recognize that many of the examples provided have suitable alternatives that can be utilized.

Fluid extravasation from IVs is known to occur primarily at two known locations (i.e., at the entry point of the catheter into the vein and at the tip of the catheter poking through an inadvertent hole in the vein). Advantageously, this disclosure describes placing extravasation detection sensors adjacent these two locations. The present IV extravasation detection device uses two or more thermometers as the fluid extravasation sensors.

Figure 1:
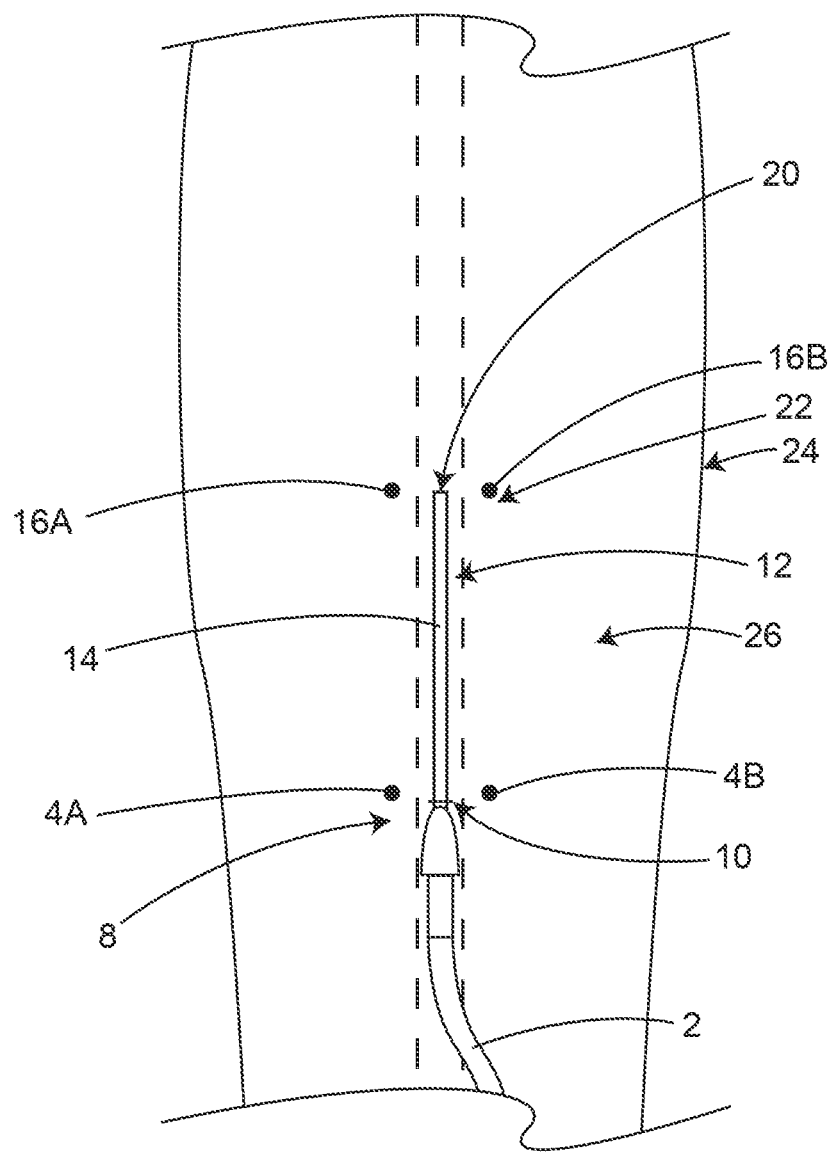
FIG. 1 shows an illustrative fluid extravasation detection device in use, with its first and second temperature sensors positioned on skin of a patient.
Figure 2:
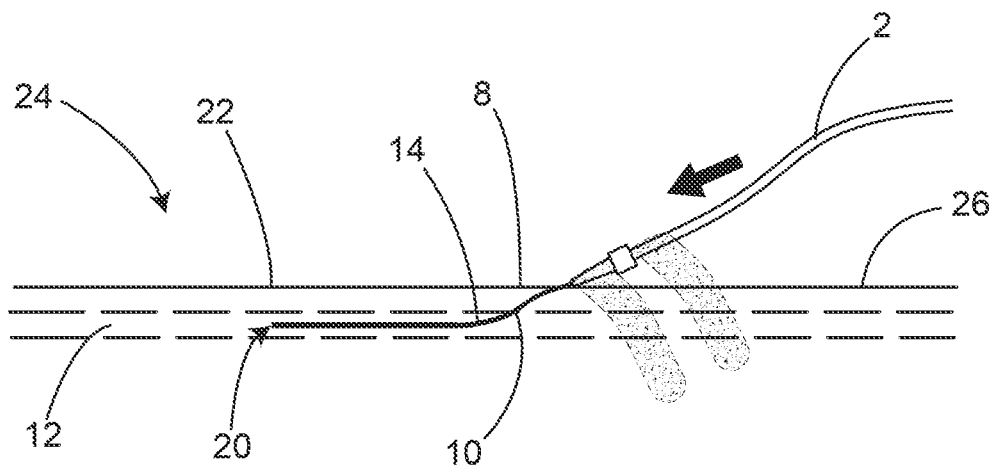
FIG. 2 shows attachment of an IV catheter to skin of a patient.

In some examples, as shown in FIG. 1, an extravasation detection device is provided that positions one or more first temperature sensors 4A, 4B, such as thermistors or thermocouples, on to the skin adjacent the entry point 10 of a catheter 14 into a vein 12 to detect a skin temperature at a first skin temperature location 8. The vein 12 in this example is in arm 24. In some examples, one or more second temperature sensors 16A, 16B are positioned on to the skin 26 adjacent the tip 20 of the catheter 14 to detect a skin temperature at a second skin temperature location 22. Since these first 8 and second 22 skin temperature locations are separated by only 4-5 cm, it is expected that the skin temperatures at these locations should be nearly identical under normal conditions. FIG. 2 also shows the first 8 and second 22 skin temperature locations.

Figure 3:
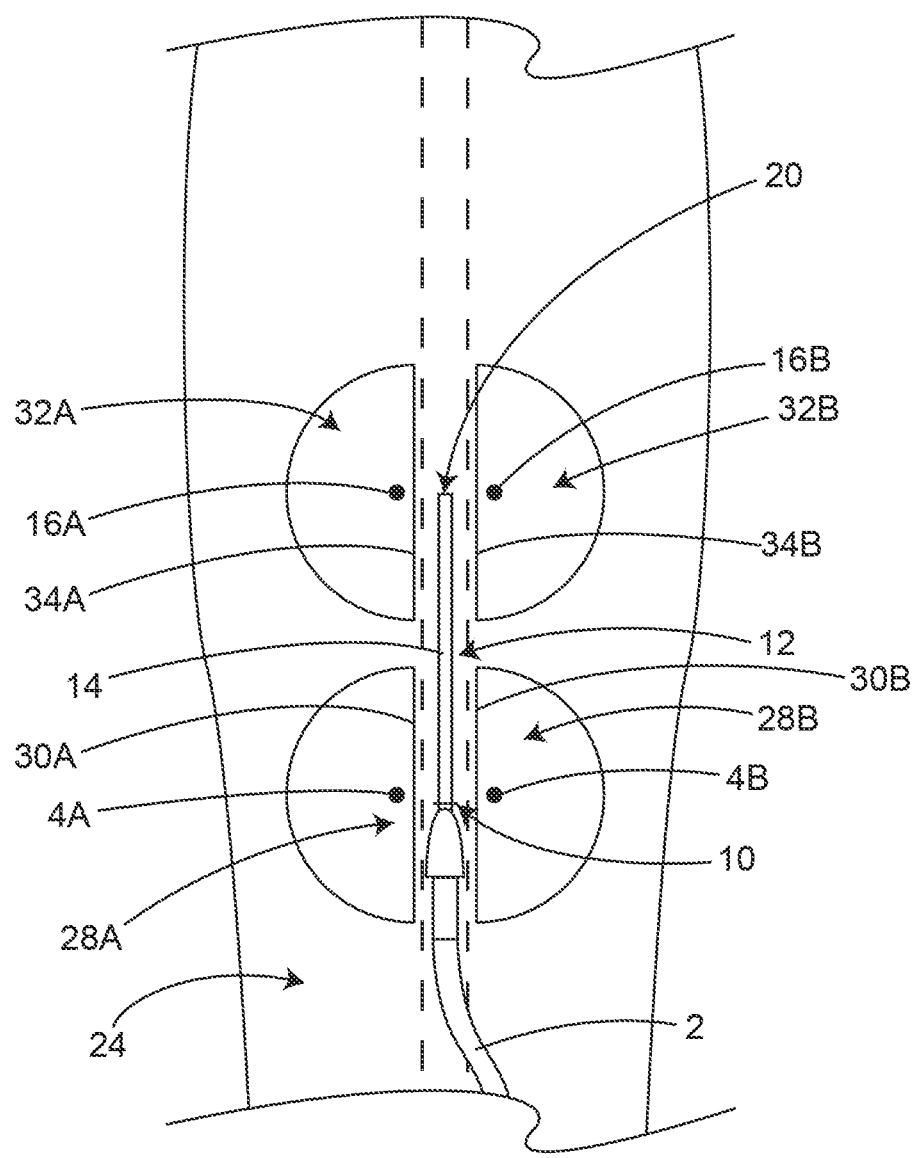
FIG. 3 shows an illustrative fluid extravasation detection device in use, with its first temperature sensors located in a first skin temperature area of a patient and the second temperature sensors located in a second skin temperature area of the patient.

In some examples, as shown in FIG. 3, the first temperature sensors 4A, 4B and the second temperature sensors 16A, 16B may be located adjacent and lateral to the vein 12. The temperature sensors 4A, 4B, 16A, 16B should not be positioned directly over vein 12 because then they would instead be responding to the intravenous fluid temperature rather than to extravasated fluid temperature. Cool or warm fluids properly flowing in the vein 12 would be sensed as a deviation in temperature and yet be perfectly normal. Therefore, in some examples, the temperature sensors 4A, 4B, 16A, 16B may be located a minimum of 0.5 cm lateral to the vein 12.

In some examples, as shown in FIG. 3, the first skin temperature areas 28A, 28B are suitable locations for sensing a first skin temperature, and the second skin temperature areas 32A, 32B are suitable locations for sensing a second skin temperature. The first temperature sensors 4A, 4B and the second temperature sensors 16A, 16B may be located anywhere within the correlating first 28A, 28B and second 32A, 32B skin temperature areas. In some examples, as shown in FIG. 3, the first and second skin temperature areas 28A, 28B, 32A, 32B are generally semicircular and can have a radius of up to 3 cm. The straight sides 30A, 30B, 34A, 34B of such semicircles can be oriented parallel to the vein 12 and catheter 14. In some examples, the straight sides 30A, 30B, 34A, 34B of the semicircles are positioned a minimum of 0.5 cm lateral to the vein 12. In such cases, the mid position of the straight sides 30A, 30B of the first skin temperature areas 28A, 28B are located approximately lateral to the entry point 10 of the catheter 14 into the vein 12. In addition, the mid position of the straight sides 34A, 34B of the second skin temperature areas 32A, 32B are located approximately lateral to the tip 20 of the catheter 14.

In some examples, the first 4A, 4B and second 16A, 16B skin temperature sensors are operably connected to an electronic thermometer that can compare a difference between the first skin temperature (at the first skin location 8) and the second skin temperature (at the second skin location 22), over time. In some examples, the two or more temperature sensors (e.g., thermistors or thermocouples) may advantageously not be calibrated in order to save costs. The two or more temperature sensors (e.g., thermistors or thermocouples) may therefore indicate slightly different temperatures even though the skin at the first and second skin temperature locations are the same temperature. In this case, the starting delta between the first and second skin temperatures would be the baseline temperature delta ($\Delta T$). Since IV fluids are virtually never the same temperature as the arm that they are being infused into, any change in the baseline $\Delta T$ between the two or more temperature sensors most likely indicates fluid extravasation either at the entry point of the catheter 14 into the vein 12 or through a hole in the vein 12 at the catheter tip 20.

In some examples, if the temperature difference between the first and second skin temperatures changes over time by more than a predetermined (e.g., preprogrammed) threshold (0.2° C., for example), an alarm may be activated. The alarm may be audio and/or visual. In some examples, the predetermined threshold $\Delta T$ may be anywhere between 0.1° C. and 2.0° C., although other temperature ranges are anticipated. A change in the first or second skin temperatures indicates that cold or warm fluids may be extravasating from either the entry point 10 of the catheter 14 into the vein 12 or from the vein 12 at the tip 20 of the catheter 14. The extravasating cold or warm fluids cause the adjacent one or more temperature sensors to be cooler or warmer than the one or more temperature sensors adjacent the non-extravasating portion of the catheter 14. Therefore, any change in the baseline $\Delta T$ can be visually investigated by the caregiver, for the possibility of IV extravasation.

IV fluids are virtually never the same temperature as the arm that they are being infused into. The vast majority of IV fluids are infused at room temperature, which ranges from 18-21° C., when they enter the body. Warmed IV fluids being rapidly administered during surgery are usually around 37° C. Slowly infused fluids, even if warmed, will cool to near room temperature before entering the patient. The typical patient's arm temperature during surgery may be 28-32° C. Therefore, in most instances, the IV fluids are 5-10° C. colder or warmer than the arm that they are being infused into.

For example, an initial first skin temperature may be 31.0° C. and a second skin temperature may be 31.2° C. In this case, 31.2° C. minus 31.0° C. equals a baseline $\Delta T$ of 0.2° C. In this example, the predetermined $\Delta T$ threshold may be 0.2° C. and therefore, if the $\Delta T$ decreases to 0.0° C. or increases to 0.4° C., an alarm may be activated.

In the rare event that the infused fluids are the same temperature as the patient's arm, the subcutaneously located extravasated fluids will compromise the blood flow to the skin due to the pressure in the subcutaneous space compressing the blood vessels supplying blood flow to the skin. The skin in that region will cool due to the reduced blood flow, relative to the rest of the arm. Therefore, even if the extravasated fluids do not directly change the local skin temperature, the result of the extravasated fluids on the normal cutaneous blood flow will indirectly change the local skin temperature.

Figure 4:
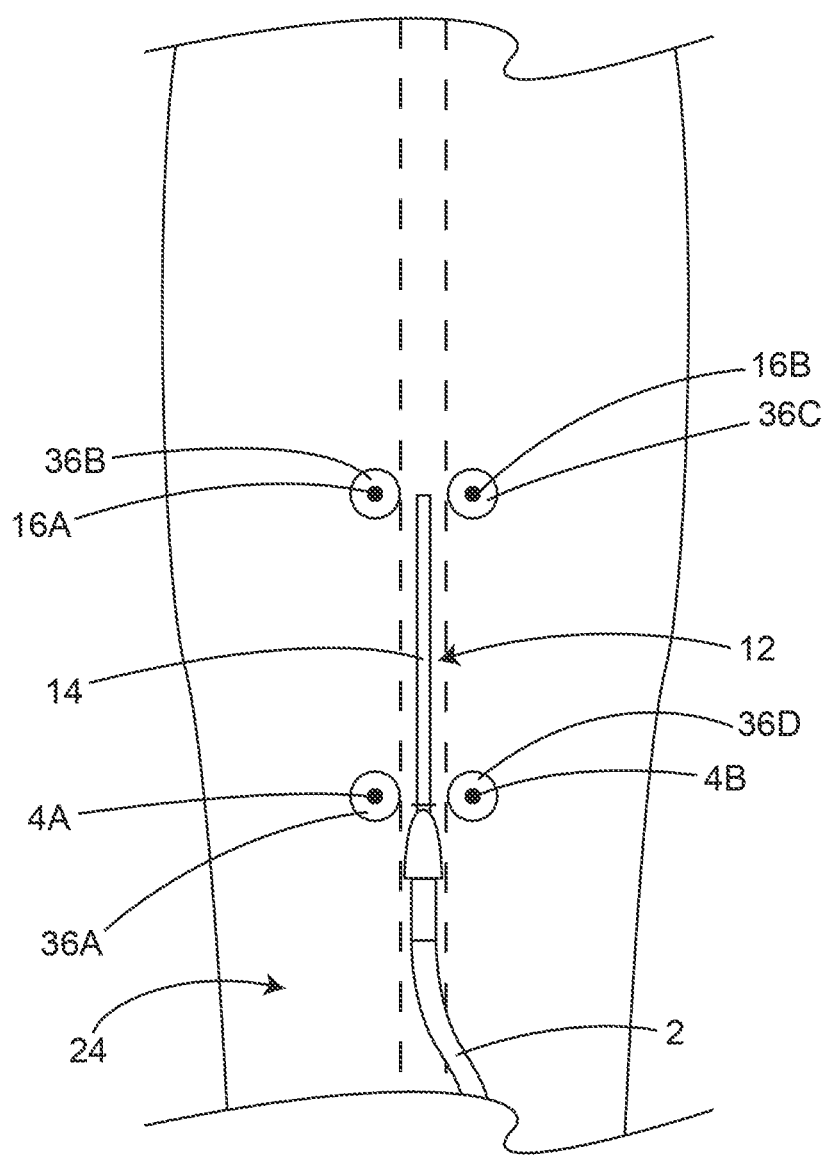
FIG. 4 shows an illustrative fluid extravasation detection device in use, with its first and second temperature sensors each attached to an anchoring platform.
Figure 5:
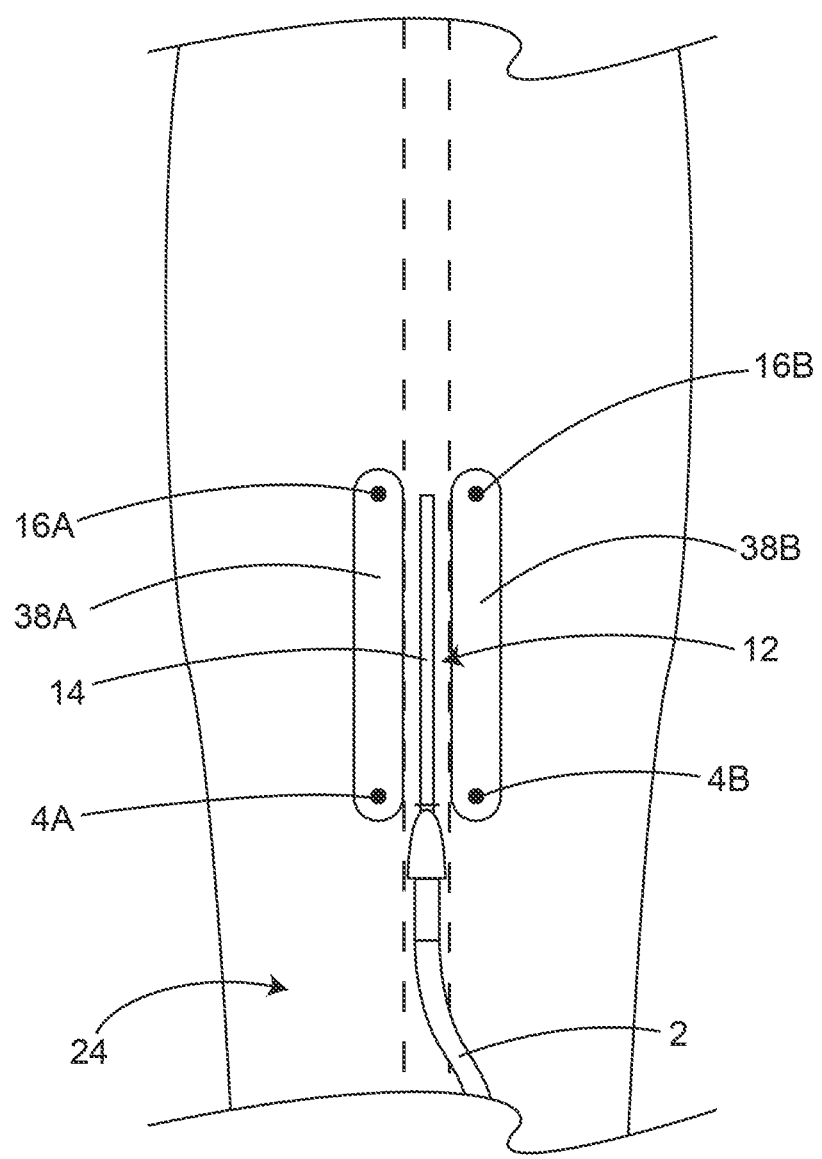
FIG. 5 shows another illustrative fluid extravasation detection device similar to FIG. 4, except that FIG. 5 shows a device having an alternative type of anchoring platform.

In some examples, as shown in FIGS. 4 and 5, the one or more first temperature sensors 4A, 4B and the one or more second temperature sensors 16A, 16B are attached to one or more anchoring platforms 36A, 36B, 36C, 36D, 38A, 38B to aid in the stabilization, location and attachment of the respective temperature sensor to the skin. In some examples, the anchoring platform(s) are relatively thin flat pieces of plastic that can be molded into a circular shape (see, e.g., anchoring platforms 36A, 36B, 36C, 36D) or an elongate shape (see, e.g., anchoring platforms 38A, 38B). Other shapes and materials are anticipated for the anchoring platforms and are within the scope of the present disclosure. The anchoring platforms 36A, 36B, 36C, 36D and 38A, 38B can include adhesive on their bottom side for attachment to the skin 26.

In some examples, one or more holes may perforate each anchoring platform to serve as a mounting location for the one or more first temperature sensors 4A, 4B and the one or more second temperature sensors 16A, 16B. Locating the skin temperature sensors in the holes allows the sensors to be in direct thermal contact with the skin below. The anchoring platforms 36A, 36B, 36C, 36D or 38A, 38B may then be adhesively attached to the skin adjacent the subcutaneously located IV catheter 14.

Figure 12:
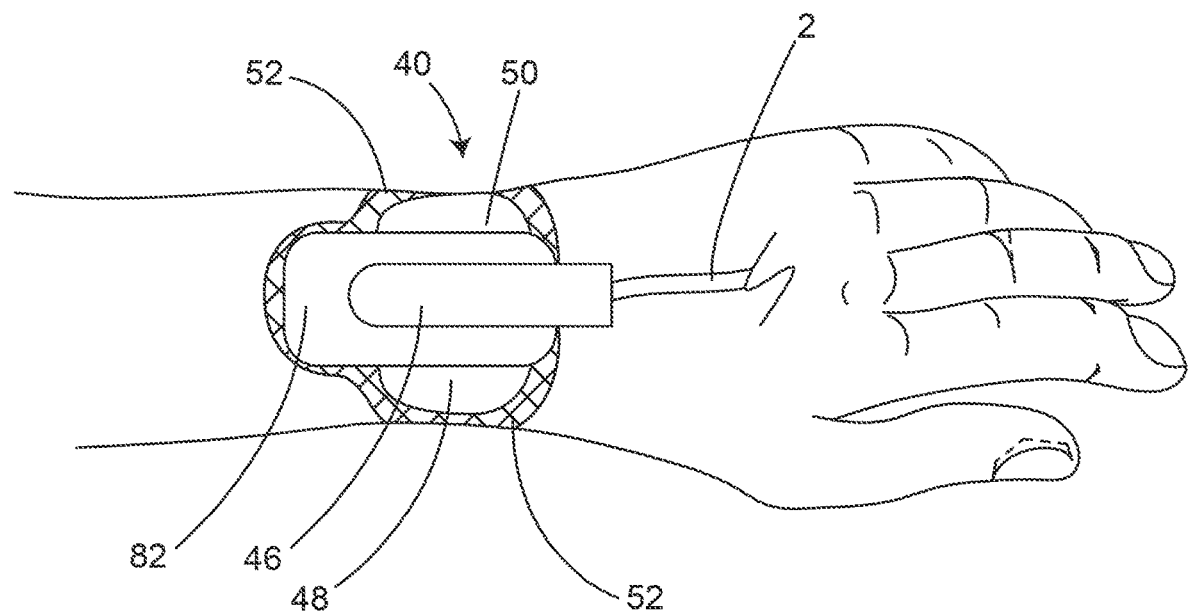
FIG. 12 is a top view of an illustrative fluid extravasation detection device.

In some examples, a small piece of metal foil, such as copper or aluminum, is attached to the underside of the anchoring platforms 36A, 36B, 36C, 36D or 38A, 38B that are covering the temperature sensor. The metal foil serves as a heat spreader to improve the thermal contact between the skin and the sensor. In some examples, as shown in FIG. 12, a layer of thermally insulating foam 82 is attached to the top side of each of the anchoring platforms 36A, 36B, 36C, 36D, 38A, or 38B (or to the top side of the catheter anchoring device 40) over the respective temperature sensor, in order to thermally insulate the temperature sensors 4A, 4B, 16A, 16B from environmental temperature influences. The layer of thermally insulating foam 82 may be a closed cell foam that may be 0.125-0.5 inches thick.

In some examples, this disclosure includes a method of detecting the subcutaneous extravasation of fluids from a vein containing an intravenous (IV) catheter. The method can include adhesively attaching one or more first temperature sensors to the skin near the entry point of the IV catheter into the vein. The method can further include adhesively attaching one or more second temperature sensors to the skin near the tip of a subcutaneously located IV catheter. The method can also include operably connecting the one or more first and one or more second temperature sensors to an electronic thermometer that compares the temperature differences between a first temperature and a second temperature over time. The first temperature is determined based on temperature detected by at least one of the one or more first temperature sensors, and the second temperature is determined based on temperature detected by at least one of the one or more second temperature sensors. In embodiments where there is more than one first temperature sensor and more than one second temperature sensor, the first temperature can be an average of the temperatures detected by the first temperature sensors, and the second temperature can be an average of the temperatures detected by the second temperature sensors. In such cases, a processor can be used to calculate such temperature averages. An alarm is activated if the temperature difference between the first temperature and the second temperature changes more than a predetermined amount over time.

Figure 6:
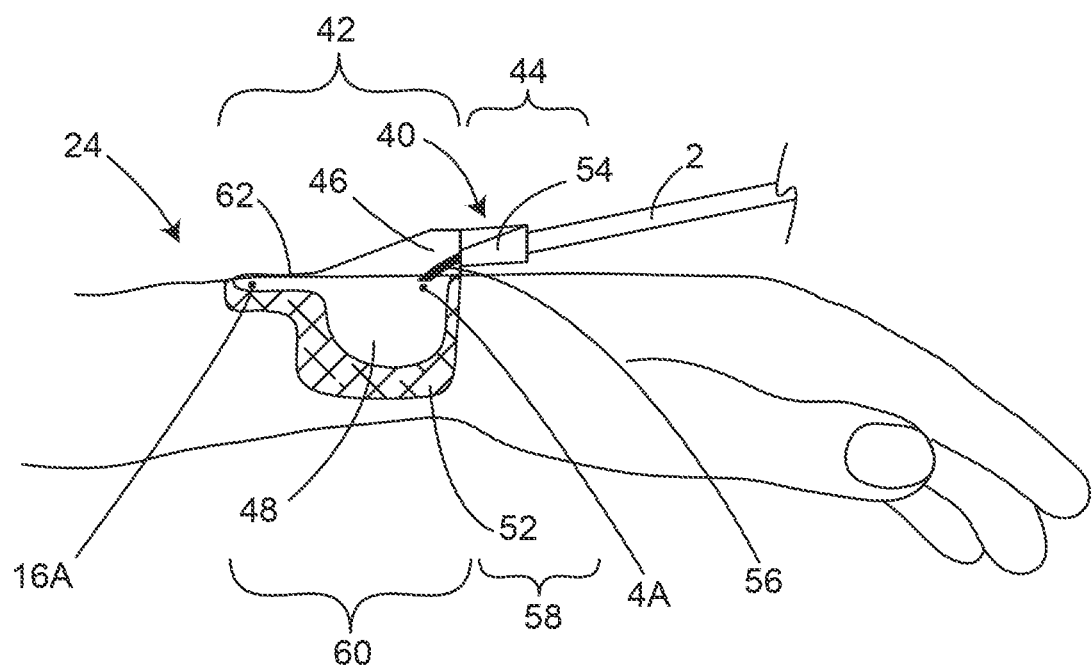
FIG. 6 is a side view of an illustrative embodiment of an illustrative fluid extravasation detection device, with a catheter anchoring device serving as the anchoring platform and attaching the first and second temperature sensors to skin of a patient.
Figure 7:
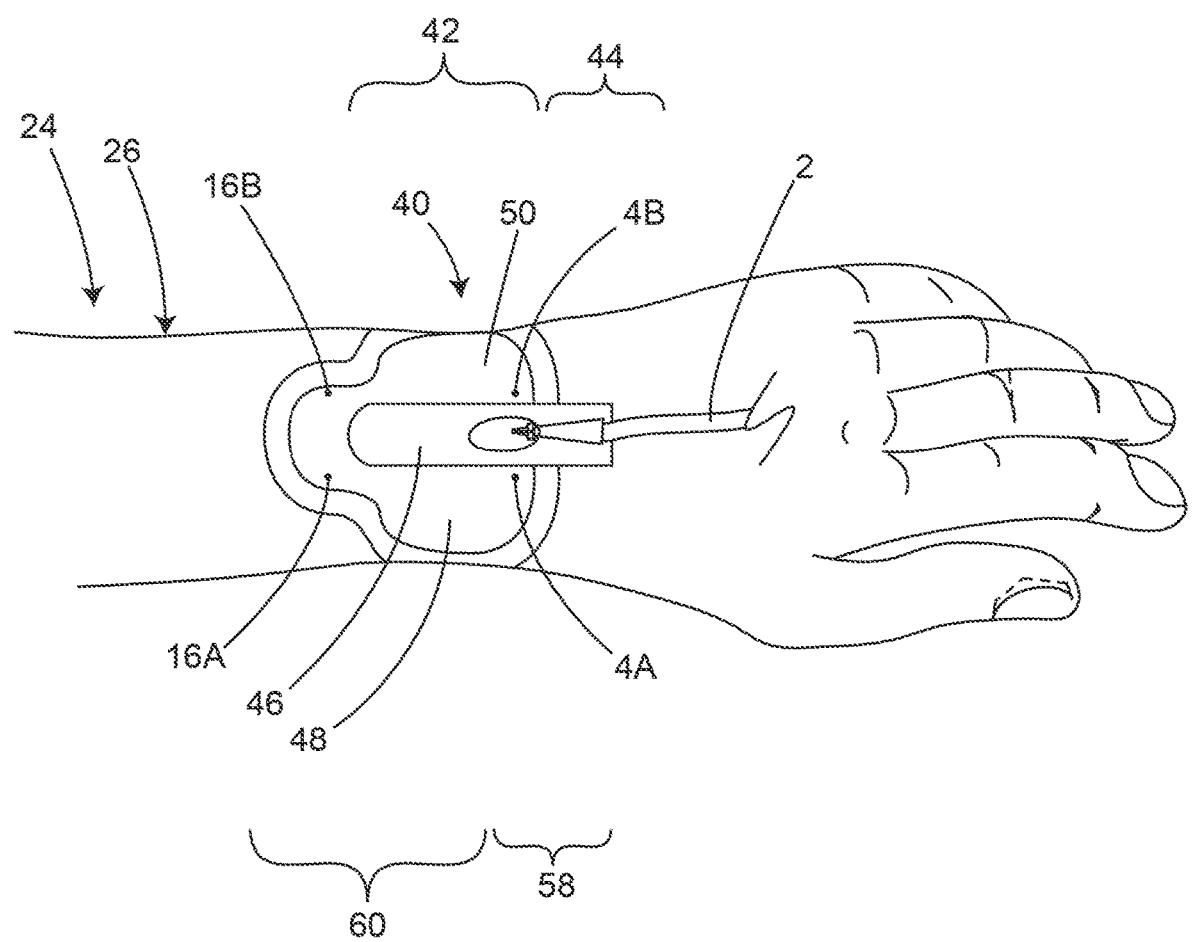
FIG. 7 is a top view of the illustrative fluid extravasation device of FIG. 6, showing the catheter anchoring device attaching the first and second temperature sensors to skin of the patient.
Figure 8:
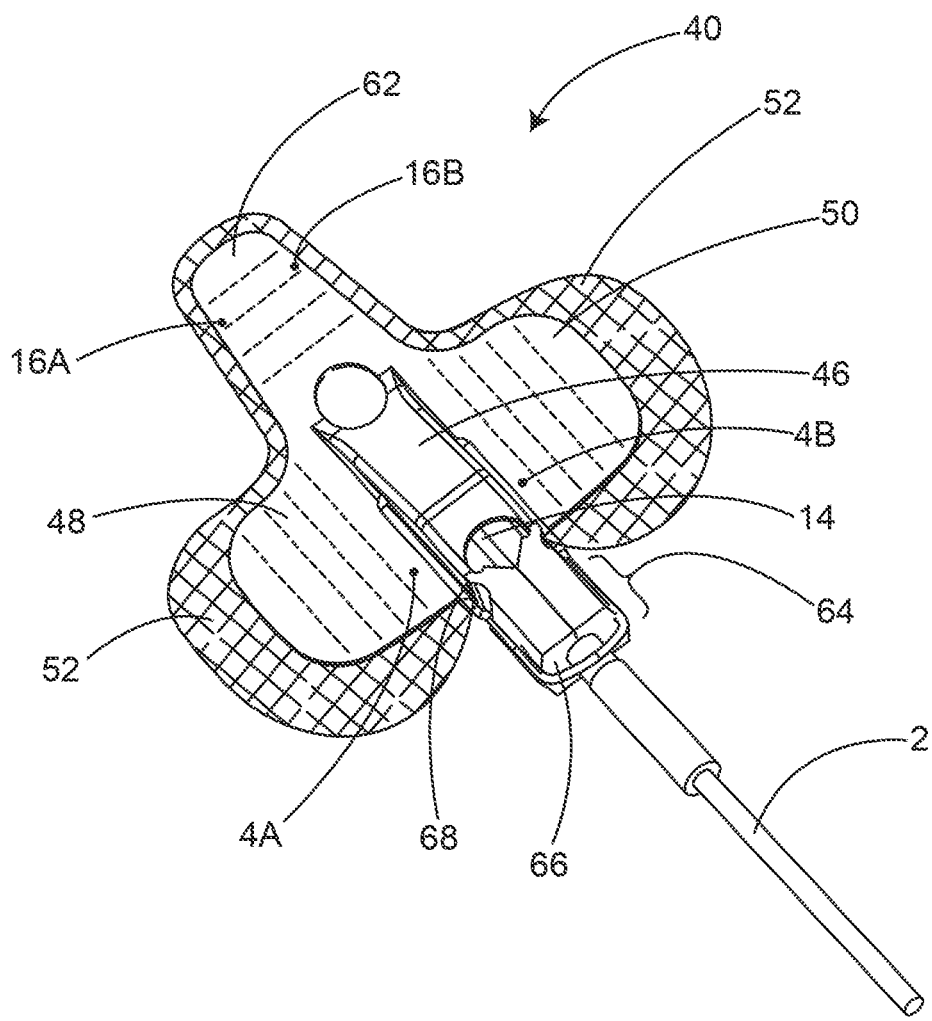
FIG. 8 is a top perspective view of an illustrative fluid extravasation detection device, with a catheter anchoring device attaching the first and second temperature sensors to skin of a patient.

In some examples, as shown in FIGS. 6, 7 and 8, the two or more skin temperature sensors 4A, 4B, 16A, 16B are attached to an IV catheter anchoring device 40 that serves a similar purpose as the anchoring platforms 36A, 36B, 36C, 36D and 38A, 38B described elsewhere herein. In some examples, the IV catheter anchoring device 40 includes a skin attachment portion 42 that can be made of flat, molded plastic and that can be adhesively attached to the skin 26 adjacent the subcutaneously located IV catheter 14.

In some examples, as shown in FIGS. 6, 7 and 8, the IV catheter anchoring device 40 that serves the same purpose as the anchoring platforms 36A, 36B, 36C, 36D and 38A, 38B, is primarily attached to the skin 26 over-laying and lateral to the subcutaneously located IV catheter 14. The location of the skin attachment portion 42 is on an opposite side of the skin puncture site 56 from conventional catheter anchors that all attach to the skin adjacent the catheter capture portion 44.

Some examples of the catheter anchoring device 40 of the instant disclosure comprise two portions, including the skin attachment portion 42 and the catheter capture portion 44. The skin attachment portion 42 is coupled to the catheter capture portion 44.

In some embodiments, the skin attachment portion 42 includes a structural body 46 and one or more skin attachment wings 48 and 50. The skin attachment portion 42 may also include an adhesive layer 52 interposed between the patient's skin 26 and the structural body 46 and the skin attachment wings 48, 50 when in use.

The skin attachment portion 42 attaches to the skin 26 of the arm 24 above and lateral to the subcutaneously located catheter (e.g., at 60). This is on the opposite side of the skin puncture site 56 compared to conventionally known methods of attaching to the skin 26 of the arm 24 adjacent the catheter hub 54 (e.g., at 58).

In some embodiments, the catheter capture portion 44 is attached to the structural body 46 and extends to the opposite side of the skin puncture site 56 in order to capture and hold the catheter hub 54. A key aspect to this catheter anchoring device 40 is that it does not need to be attached to the skin 26 of the arm adjacent to catheter hub 54 (e.g., at 58). In some embodiments, there may be a loose attachment to the skin 26 of the arm 24 adjacent the catheter 14. However, the principal attachment of the catheter anchoring device 40 is to the skin 26 of the arm 24 above and lateral to the subcutaneously located IV catheter 14 (e.g., at 60 in FIGS. 6 and 7). This design allows the catheter hub 54 to be securely captured and held, yet remain relatively independent of the skin 26 of the arm 24 adjacent the catheter hub 54 (e.g., at 58).

In other words, the catheter anchoring device 40 for securing percutaneous medical catheters to the skin 26 of the body may include the catheter capture portion 44 and the skin attachment portion 42. The catheter capture portion 44 may be configured to engage with a portion of the catheter 14 protruding from the skin 26 after percutaneous placement of the catheter 14 into the body.

In some embodiments, the skin attachment portion 42 has an upper surface (e.g., a first surface), a lower surface (e.g., a second surface), and an adhesive layer 52. The upper surface is configured to face away from the skin 26 of the body (e.g., to arm 24) when the catheter anchoring device 40 is positioned to anchor the catheter 14 to the body (e.g., to arm 24). The lower surface is located opposite the upper surface and is configured to face the skin 26 of the body when the catheter anchoring device 40 is positioned to anchor the catheter 14 to the body (e.g., to arm 24). The adhesive layer 52 may be disposed on the lower surface. The adhesive layer may be configured to adhesively attach the lower surface of the skin attachment portion 42 to the skin 26. In some embodiments, the adhesive layer 52 is disposed on the lower surface of the skin attachment portion 42 and is configured to anchor the catheter anchoring device 40 to the body at the skin 26 overlaying the subcutaneously located IV catheter 14 and lateral to the subcutaneously located IV catheter 14 (e.g. at 60 in FIGS. 6 and 7).

In some examples of the catheter anchoring device 40, when the adhesive layer 52 is applied to the skin 26 to anchor the device 40, a second portion of the catheter, or IV tubing 2 that may extend outside of the catheter hub 54 (if provided) and away from the skin puncture site 56, is located more distal from the skin 26 (e.g., at 58 in FIGS. 6 and 7) than the adhesive layer 52.

As shown in FIGS. 6 and 8, in some examples, this catheter anchoring device 40 includes a structural body 46 that forms the "backbone" of the device 40 and substantially overlays the subcutaneously located IV catheter 14. In some embodiments, the structural body 46 comprises a "half pipe" structure with a rounded upper surface and the open interior straddling and parallel to the subcutaneously located IV catheter 14. The structural body 46 provides longitudinal rigidity to the device 40 for transferring forces from the catheter capture portion 44 to the skin attachment portion 42. In some examples, the structural body 46 lies substantially in the center of the skin attachment portion 42 area, effectively creating a "center of effort" for externally applied force dissipation.

In some examples, two or more skin attachment wings 48, 50 are attached to the lateral sides of the structural body 46. One of the key features of the skin attachment wings 48, 50 is that they must be flexible enough to conform to the contours of the patient's body and yet stiff enough to provide stability to the structural body 46 of the catheter anchoring device 40. In some embodiments, the skin attachment wings 48, 50 are made of a layer of plastic material.

The skin attachment wings 48, 50, are designed to provide a larger surface for adhesion of the catheter anchoring device 40 to the skin 26. In some embodiments, an adhesive layer 52 is applied to the lower surface of the skin attachment wings 48, 50 for adhering the skin attachment wings to the patient's skin 26. In some embodiments, the adhesive layer 52 is applied to the lower surface of the skin attachment wings 48, 50, and then the adhesive layer 52 (e.g., adhesive tape) adheres to the patient's skin 26, as shown in FIGS. 6 and 7.

In some examples, the adhesive layer 52 is disposed on the lower surface of the skin attachment wings 48, 50 and is configured to adhesively attach the lower surface of the skin attachment wings 48, 50 to the skin 26 such that the skin attachment portion 42 is configured to anchor the catheter anchoring device 40 to the body at the skin 26 overlaying the subcutaneously located IV catheter 14 and lateral to the subcutaneously located IV catheter 14.

In some examples, as shown in FIGS. 6-8, the catheter anchoring device 40 includes a third (longitudinal) skin attachment wing 62 extending longitudinally from the structural body 46 and overlaying the tip 20 of the subcutaneously located IV catheter 14. The construction of the longitudinal skin attachment wing 62 may be similar to the skin attachment wings 48, 50. The longitudinal skin attachment wing 62 also has an adhesive layer 52 applied to its lower side that may be attached to the patient's skin 26, such as a layer of adhesive tape which may be attached to the patient's skin 26.

In some examples, the purpose of the longitudinal skin attachment wing 62 is to provide added stability to the catheter anchoring device 40. Additionally, since the longitudinal skin attachment wing 62 adhesively attaches to the skin 26 overlaying the tip 20 of the subcutaneously located IV catheter 14, a movement of the catheter anchoring device 40 and catheter 14 will cause a similar movement of the skin 26 overlaying the subcutaneous catheter tip 20, and a similar movement of the vein 12 that is loosely attached to the skin 26 overlaying the tip 20. The longitudinal skin attachment wing 62 attached to the skin 26 overlaying the catheter tip 20 is therefore advantageous in order to move the skin 26 overlaying the catheter tip 20, the vein 12, and the catheter tip 20, all simultaneously in the same direction in response to a movement of the catheter hub 54 or IV tubing 2. The longitudinal skin attachment wing 62 has a stiffness that allows for "pushing" the skin 26 as well as "pulling" the skin 26, in contrast to plastic film bandages that can only "pull" the skin 26. The simultaneous movement of the catheter 14 and vein 12 clearly reduces the probability of the catheter tip 20 inadvertently poking through the fragile wall of the vein 12 as a result of inadvertent movement of the catheter 14, in contrast to conventional catheter devices.

In some examples, and as shown in FIGS. 6, 7 and 8, an adhesive layer 52 such as a layer of adhesive tape, is located between each of the skin attachment wings 48, 50, and the patient's skin 26. In this case, the skin attachment wings 48, 50 are bonded to the adhesive layer 52. The bond may be an adhesive bond, a solvent bond, or a thermal bond such as a heat seal, an RF seal, or an ultrasound seal.

In some embodiments, the adhesive layer 52 is made of fabric, foam, plastic film, fiber reinforced film, or any other suitable adhesive layer. The attachment of the adhesive layer 52 to the patient's skin 26 may be an adhesive that can be softened or dissolved with alcohol for easy removal from the skin. Other adhesives are anticipated, including but not limited to, hydrogels and hydrocolloids. The adhesive layer 52 may advantageously include nonstick release liners applied over the adhesive surface that can be removed at the time of application to the patient. The adhesive layer 52 may be configured to adhesively attach the catheter anchoring device 40 to the skin 26, wherein more than 50% of the adhesive surface of the skin attachment portion 42 is attached to the skin overlaying and lateral to the subcutaneously located IV catheter 14 (e.g., 60). In a preferred embodiment, more than 70% of the adhesive surface is configured to attach as described, and in a more preferred embodiment, more than 85% of the adhesive surface is configured to attach as described. This adhesive arrangement provides a secure connection of the catheter anchoring device 40 to the skin 26.

In some embodiments, as shown in FIG. 8, the catheter capture receptacle 64 comprises two pieces of half shell 66 molded plastic that "clamshell" together around the catheter hub 54 or the catheter 14. In some embodiments, the "clamshell" action can occur because of two vertically oriented hinges 68 molded at the junction between the two half shells 66 and the structural body 46 of the skin attachment portion 42. The hinge 68 may each be a "living hinge," which is a thinned line in a molded plastic part that promotes bending or hinging at that location. The hinges 68 can allow the two half shells 66 to swing horizontally closed from the sides as shown in FIG. 8. This allows the catheter capture receptacle 64 to close around the catheter hub 54 or the catheter 14 positively controlling the catheter hub 54, preventing its movement in any direction. The horizontal closing of the half shells 66 allows the capture of the catheter hub 54 without displacing the newly inserted catheter by lifting it. This is in contrast to tape and conventional anchoring devices, all of which require that the catheter hub 54 be elevated off of the skin 26 so that the tape or anchoring device can be inserted between the catheter hub 54 and the skin 26. This lifting movement of the catheter hub 54 obviously increases the probability of dislodgment of the catheter 14 during the securing procedure.

Similar to the anchoring platforms 36A, 36B, 36C, 36D, 38A, 38B of this disclosure, the skin attachment portion 42 of an IV catheter anchoring device 40 may include two or more holes that serve as a mounting location for the two or more skin temperature sensors 4A, 4B, 16A, 16B. Locating the skin temperature sensors in the holes allows the sensors to be in direct thermal contact with the skin below. The skin attachment portion 42 may then be adhesively attached to the skin adjacent the subcutaneously located IV catheter 14.

In some examples, a small piece of metal foil, such as copper or aluminum, is attached to the underside of the skin attachment portion 42 of the catheter anchoring device 40 covering the temperature sensors 4A, 4B, 16A, 16B. The metal foil serves as a heat spreader to improve the thermal contact between the skin and the temperature sensors 4A, 4B, 16A, 16B. In some examples, as shown in FIG. 12, a layer of thermally insulating foam 82 is attached to the top side of the skin attachment wings 48, 50 of the catheter anchoring device 40 over the respective temperature sensor, in order to thermally insulate the temperature sensors 4A, 4B, 16A, 16B from environmental temperature influences. The layer of thermally insulating foam 82 may be a closed cell foam that may be 0.125-0.5 inches thick.

In some examples, using a catheter anchoring device 40 to serve as the anchoring platform is advantageous because the location of the entry point of the catheter 14 into the vein 12 and the location of the tip of the catheter 20 is known relative to the catheter anchoring device 40. Therefore, the two or more skin temperature sensors 4A, 4B, 16A, 16B can be precisely located relative to the vein 12 and catheter 14 by using predetermined locations on the catheter anchoring device 40. This allows rapid and reliable placement of the skin temperature sensors 4A, 4B, 16A, 16B in precise locations relative to the vein 12 and the catheter 14.

In some examples, the use of two or more skin temperature sensors 4A, 4B, 16A, 16B for the detection of extravasated IV fluids is beneficial. However, it must be understood that other extravasation sensors, including but not limited to, ultrasound, electrical bio-impedance, and mechanical stretching sensors, could benefit from mounting on a catheter anchoring device 40. Similar to the skin temperature sensors 4A, 4B, 16A, 16B described in this disclosure, mounting other extravasation sensors adjacent locations where extravasation is known to occur is advantageous. The exact location of the other extravasation sensors relative to the vein 12 and the catheter 14 by using predetermined locations on the catheter anchoring device 40, allows rapid and reliable placement of the other extravasation sensors in precise locations relative to the vein 12 and the catheter 14.

Figure 9:
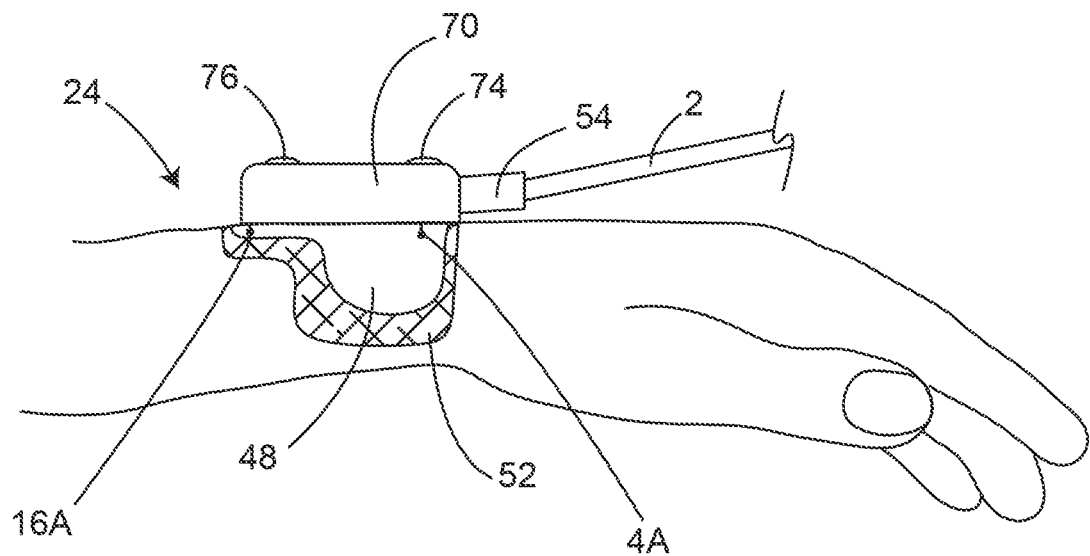
FIG. 9 is a side view of an illustrative fluid extravasation detection device having an electronic thermometer unit attached directly to the first and second temperature sensors.
Figure 10:
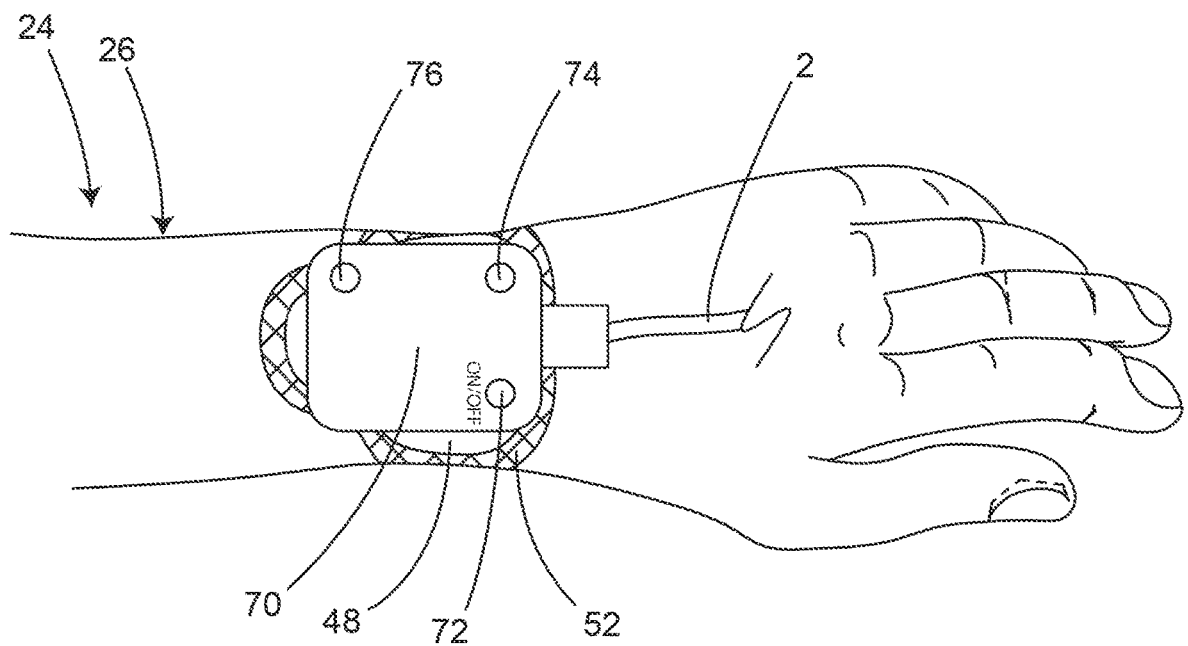
FIG. 10 is a top view of the illustrative fluid extravasation detection device of FIG. 9.
Figure 11:
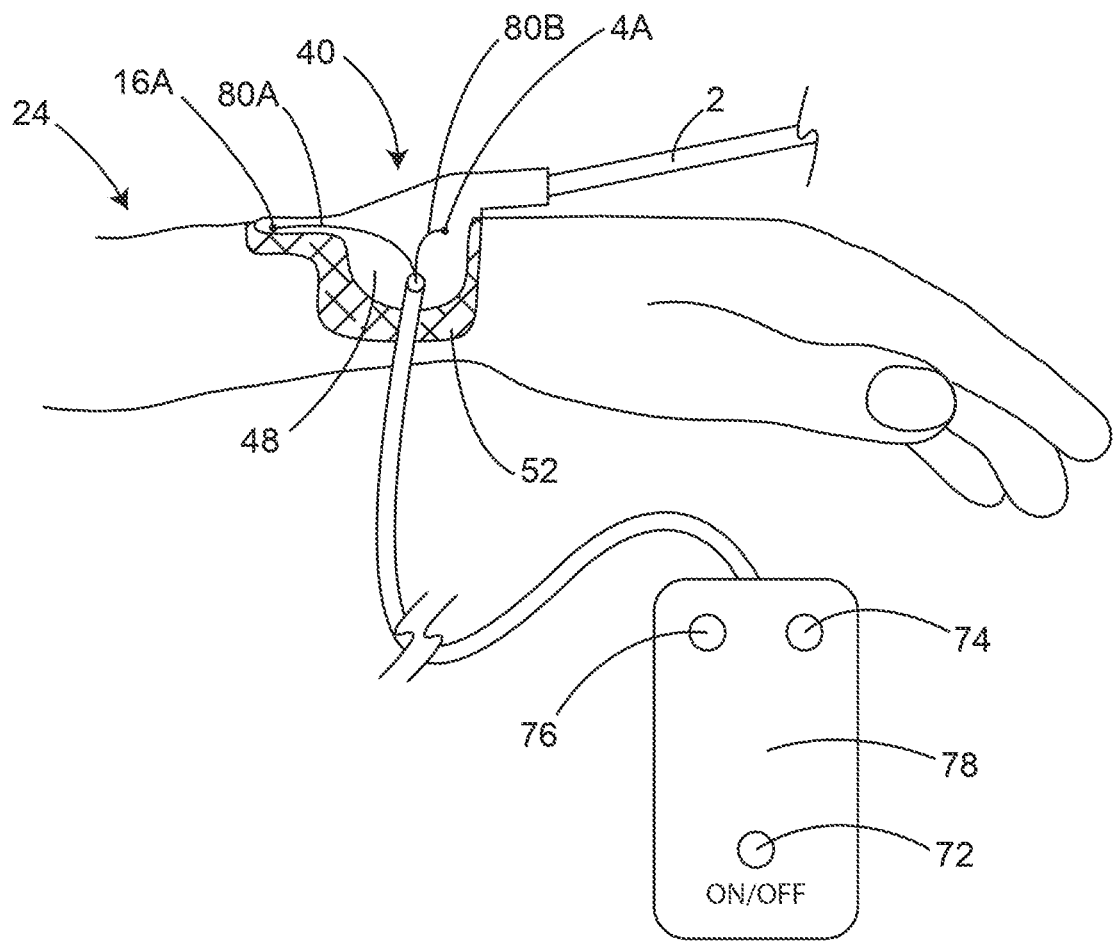
FIG. 11 is a side view of an illustrative fluid extravasation detection device having an electronic thermometer unit attached to the first and second temperature sensors by wire leads.

In some examples, as shown in FIGS. 9-11, the first temperature sensors 4A, 4B and the second temperature sensors 16A, 16B are attached either directly to a portable electronic thermometer unit 70 or by wire leads to a fixed electronic thermometer unit 78. The electronic thermometer units 70 and 78 have the capacity to read two or more temperature sensors (including temperature sensors 4A and 16A, for example) either simultaneously or in a sequential and alternating fashion.

Figure 13:
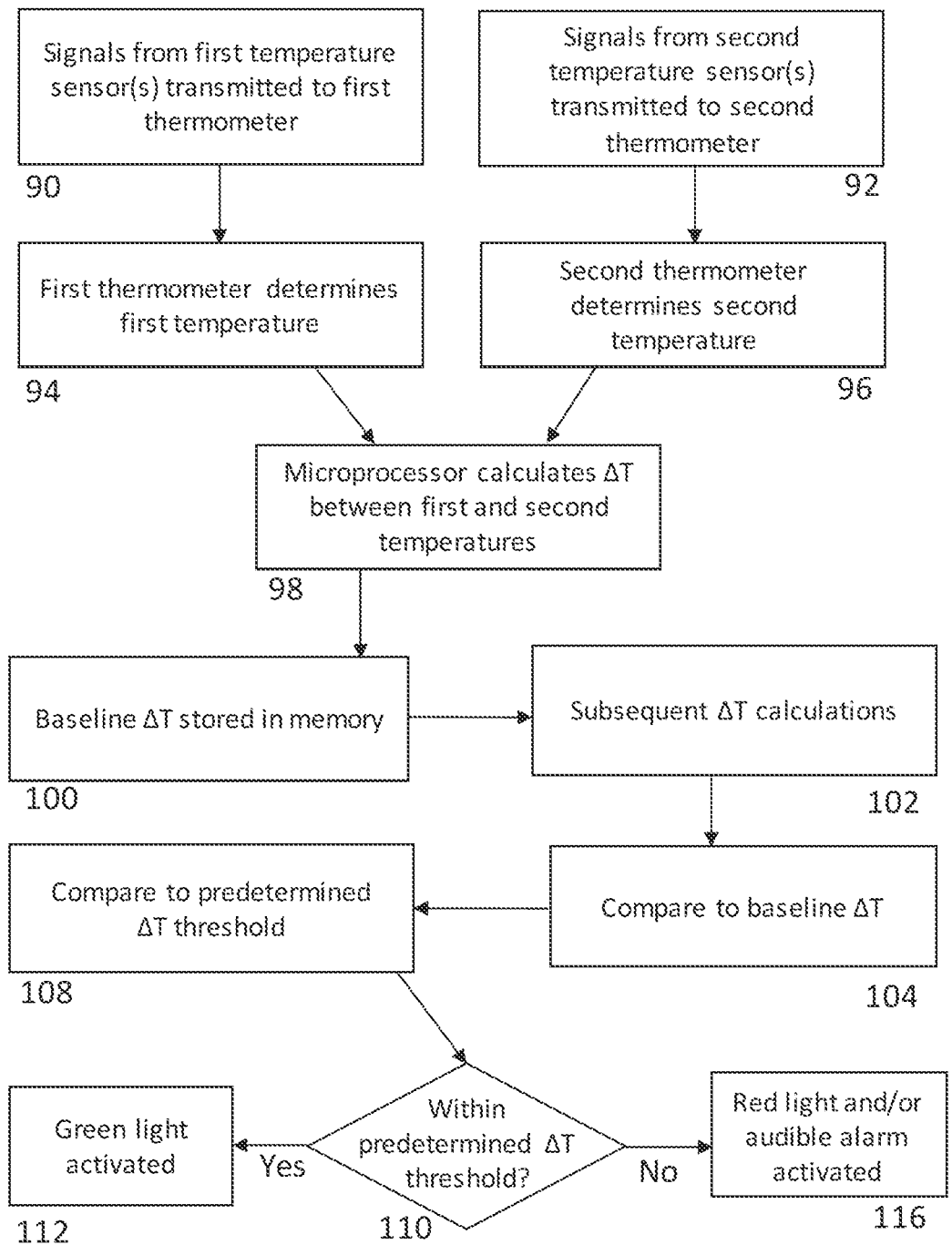
FIG. 13 is a flow diagram illustrating a method of using the illustrative fluid extravasation detection device.

FIG. 13 shows an illustrative method of using a fluid extravasation detection device. In some examples, the method includes transmitting signals from the first temperature sensor(s) to a first thermometer (step 90) and transmitting signals from the second temperature sensor(s) to a second thermometer (step 92). In some cases, the method includes the first thermometer determining the first temperature (step 94), and the second thermometer determining the second temperature (step 96). As previously discussed, the first thermometer and the second thermometer can be a single thermometer that is sequentially and alternately monitoring both the first temperature sensor and the second temperature sensor. The method can also include a step 98 of a microprocessor calculating a baseline ΔT, which is the baseline temperature difference between the first thermometer and the second thermometer. In some cases, the baseline ΔT is then stored in memory (step 100). The electronic thermometer units may also include the capacity to wait for the system to equilibrate (5-10 minutes, for example) before recording the baseline ΔT from the first temperature sensor(s) 4A, 4B and the second temperature sensor(s) 16A, 16B.

After a baseline ΔT has been determined, the microprocessor can substantially continuously calculate the temperatures from the first temperature sensor(s) and the second temperature sensor(s) (step 102). The microprocessor can then compare the subsequent ΔTs to the baseline ΔT that is stored in memory (step 104). Thereafter, the microprocessor can compare the subsequent ΔTs to a predetermined ΔT threshold (step 108) and determine if they are within a predetermined temperature threshold (step 110) that has been programmed into the microprocessor. If no (i.e., if the allowable ΔT threshold is exceeded), the microprocessor may activate a red light (or other suitable color) and/or may activate an audible alarm (step 116). In such cases, the alarm may be activated in one or both of the electronic thermometer units 70, 78 or the remotely connected monitoring station. If the allowable ΔT threshold is not exceeded, the microprocessor may activate a green light (or other suitable color) to indicate normal operating conditions (step 112).

In some examples, as shown in FIGS. 9 and 10, the electronic thermometer unit 70 may be a small battery-powered portable unit that attaches to the patient's arm 24 and is connected directly to the first temperature sensors 4A, 4B and the second temperature sensors 16A, 16B. In some cases, the electronic thermometer unit 70 attaches to the patient's arm 24 using an adhesive attachment 52. In some examples, the electronic thermometer unit 70 may be attached to a catheter anchoring device 40 that is adhesively attached to the patient's arm. In some cases, the electronic thermometer unit 70 includes an ON/OFF switch 72 and may also include indicator lights 74 and 76. For example, there may be a red indicator light 74 that illuminates during alarm conditions and a green indicator light 76 that is illuminated during normal operating conditions. An alarm condition may cause an audible alarm in the portable electronic thermometer unit 70 to be activated. In some examples, the portable electronic thermometer unit 70 may be in wireless communication with a central monitoring and alarm system and the electronic medical record (EMR). In this example, the portable electronic thermometer unit 70 may activate a central alarm at the nurses' station, for example. A small portable electronic thermometer unit 70 may be advantageous for patients that are mobile and do not wish to be tethered to a fixed monitor location.

In some examples, as shown in FIG. 11, a fixed electronic thermometer unit 78 may be detached from the patient and connected to the first temperature sensors 4A, 4B and the second temperature sensors 16A, 16B by wire leads 80A, 80B. In this instance, the monitor may be an independent unit or may be built into the patient monitoring system or an equipment module in the operating room, for example. In some examples, the fixed electronic thermometer unit 78 includes an ON/OFF switch 72 and may also include indicator lights 74 and 76. For example, there may be a red indicator light 74 that illuminates during alarm conditions and a green indicator light 76 that is illuminated during normal conditions. An alarm condition may cause an audible alarm in the fixed electronic thermometer unit 78 to be activated. In some examples, the fixed electronic thermometer unit 78 may be in wireless or hard-wired communication with a central monitoring and alarm system and the electronic medical record (EMR).

In some examples, the portable electronic thermometer unit 70 or the fixed electronic thermometer unit 78 may be in wireless or hard-wired communication with an alarm in the suite of monitors used by an anesthesiologist during surgery. One such suite of monitors is disclosed in U.S. Pat. Nos. 10,507,153 and 10,512,191, which are incorporated herein by reference in their entireties.

Inputs from the electronic thermometer and alarm to the patient monitoring system or equipment module may be automatically passed on (e.g., transmitted) for recording in the electronic anesthesia record (EAR) and/or to the electronic medical record (EMR). Documentation of IV patency is a critical and time-consuming task in many hospitals and other healthcare delivery locations. Some hospitals require hourly visual inspection and documentation of IV patency by a nurse, 24 hours a day. Automatic monitoring and documentation of IV patency saves healthcare provider time and cost.

While some preferred embodiments of the invention have been described, it should be understood that various changes, adaptations, and modifications may be made therein without departing from the spirit of the invention and the scope of the appended claims.

The invention claimed is:

1. A fluid extravasation detection device for detecting the subcutaneous extravasation of fluid from a vein containing an intravenous (IV) catheter comprising:
   one or more first temperature sensors for positioning on skin of a patient lateral and adjacent to an entry point of the IV catheter into the vein, the one or more first temperature sensors being adapted to detect a first temperature at a first skin temperature location;
   one or more second temperature sensors for positioning on skin of the patient lateral and adjacent to a tip of the subcutaneously located IV catheter, the one or more second temperature sensors being adapted to detect a second temperature at a second skin temperature location;
   a catheter anchoring device comprising:
      a skin attachment portion for holding the one or more first and the one or more second temperature sensors in contact with skin of the patient; and
      a catheter capture portion configured to engage with a portion of the catheter,
      the skin attachment portion coupled to the catheter capture portion, the skin attachment portion configured to adhesively attach the catheter anchoring device to the skin,
      the skin attachment portion comprises an adhesive surface configured to adhesively attach the catheter anchoring device to the skin, wherein more than 50% of the adhesive surface of the skin attachment portion extends beyond the catheter capture portion in a direction along the elongation of the catheter, and being positioned on opposite sides along the elongation of the catheter,
      the skin attachment portion holds the one or more first and the one or more second temperature sensors at predetermined locations on the catheter anchoring device relative to the catheter capture portion such that the one or more first temperature sensors are positioned lateral and adjacent to the entry point of the IV catheter into the vein and the one or more second temperature sensors are positioned lateral and adjacent to the tip of the subcutaneously located IV catheter;
   an electronic thermometer operably connected to the one or more first and the one or more second temperature sensors, the electronic thermometer being adapted to compare a temperature difference between the first temperature and the second temperature over time; and
   an alarm that is configured to be activated if the temperature difference between the first and second temperatures changes more than a predetermined amount over time.

2. The fluid extravasation detection device of claim 1, wherein the one or more first and one or more second temperature sensors are thermistors.

3. The fluid extravasation detection device of claim 1, wherein the one or more first and one or more second temperature sensors are thermocouples.

4. The fluid extravasation detection device of claim 1, wherein the skin attachment portion holds the one or more first temperature sensors within areas defined by one or two semicircles centered on the entry point of the IV catheter into the vein with 3 cm radii, the one or two semicircles each having a straight side oriented parallel to and at least 0.5 cm lateral to the subcutaneously located IV catheter.

5. The fluid extravasation detection device of claim 1, wherein the skin attachment portion holds the one or more second temperature sensors within areas defined by one or two semicircles centered adjacent the tip of the catheter with 3 cm radii, the one or two semicircles each having a straight side oriented parallel to and at least 0.5 cm lateral to the subcutaneously located IV catheter.

6. The fluid extravasation detection device of claim 1, wherein the alarm is activated if the temperature difference between the first and second temperatures changes more than 0.1-2.0° C. over time.

7. The fluid extravasation detection device of claim 1, wherein the skin attachment portion includes a layer of thermally insulating foam material positioned over the one or more first and one or more second temperature sensors to insulate the first and second temperature sensors from environmental temperature influences.

8. The fluid extravasation detection device of claim 1, wherein all of the first and second temperature sensors are configured to be positioned adjacent to, and laterally spaced from, the vein.

9. The fluid extravasation detection device of claim 1, wherein each of the second temperature sensors are configured to be positioned not closer than 0.5 cm to the vein and not further than 3.0 cm from the vein.

10. A fluid extravasation detection device for detecting the subcutaneous extravasation of fluid from a vein containing an intravenous (IV) catheter comprising:
   a catheter anchoring device that includes a catheter capture portion configured to engage with a portion of an IV catheter and a skin attachment portion coupled to the catheter capture portion, the skin attachment portion configured to adhesively attach the catheter anchoring device to skin of a patient, the skin attachment portion comprises an adhesive surface configured to adhesively attach the catheter anchoring device to the skin overlaying the IV catheter when the IV catheter is located subcutaneously, wherein the skin attachment portion is sized and positioned to overlay substantially the entire subcutaneously located catheter;

one or more first temperature sensors for positioning on skin lateral and adjacent to an entry point of the IV catheter into the vein and the one or more first temperature sensors are held in thermal contact with the skin by attachment to the skin attachment portion of the catheter anchoring device, the one or more first temperature sensors being adapted to detect a first temperature at a first skin temperature location;

one or more second temperature sensors for positioning on skin lateral and adjacent to a tip of the subcutaneously located IV catheter, and the one or more second temperature sensors are held in thermal contact with the skin by attachment to the skin attachment portion of the catheter anchoring device, the one or more second temperature sensors being adapted to detect a second temperature at a second skin temperature location;

an electronic thermometer operably connected to the one or more first and one or more second temperature sensors, the electronic thermometer being adapted to compare a temperature difference between the first temperature and the second temperature over time; and an alarm that is configured to be activated if the temperature difference between the first and second temperatures changes more than a predetermined amount over time; and wherein the skin attachment portion holds the one or more first and the one or more second temperature sensors at predetermined locations on the catheter anchoring device relative to the catheter capture portion such that the one or more first temperature sensors are positioned lateral and adjacent to the entry point of the IV catheter into the vein and the one or more second temperature sensors are positioned lateral and adjacent to the tip of the subcutaneously located IV catheter.

11. The fluid extravasation detection device of claim 10, wherein the one or more first and one or more second temperature sensors are thermistors.

12. The fluid extravasation detection device of claim 10, wherein the one or more first and one or more second temperature sensors are thermocouples.

13. The fluid extravasation detection device of claim 10, wherein the skin attachment portion holds the one or more first temperature sensors within areas defined by one or two semicircles centered on the entry point of the IV catheter into the vein with 3 cm radii, the one or two semicircles each having a straight side oriented parallel to and at least 0.5 cm lateral to the subcutaneously located IV catheter.

14. The fluid extravasation detection device of claim 10, wherein the skin attachment portion holds the one or more second temperature sensors within areas defined by one or two semicircles centered adjacent the tip of the catheter with 3 cm radii, the one or two semicircles each having a straight side oriented parallel to and at least 0.5 cm lateral to the subcutaneously located IV catheter.

15. The fluid extravasation detection device of claim 10, wherein the alarm is activated if the temperature difference between the first and second temperatures changes more than 0.1-2.0° C. over time.

16. The fluid extravasation detection device of claim 10, wherein the skin attachment portion includes a layer of thermally insulating foam material positioned over the one or more first and one or more second temperature sensors to insulate the first and second temperature sensors from environmental temperature influences.

17. The fluid extravasation detection device of claim 10, wherein all of the first and second temperature sensors are configured to be positioned adjacent to, and laterally spaced from, the vein.

18. A fluid extravasation detection device for detecting the subcutaneous extravasation of fluid from a vein containing an intravenous (IV) catheter comprising:

a catheter anchoring device that includes a catheter capture portion configured to engage with a portion of an IV catheter and a skin attachment portion coupled to the catheter capture portion, the skin attachment portion configured to adhesively attach the catheter anchoring device to skin of a patient, wherein the skin attachment portion is sized and positioned to attach to the skin adjacent to both sides and a tip of the IV catheter when the IV catheter is located subcutaneously;

one or more first temperature sensors for positioning on skin lateral and adjacent to an entry point of the IV catheter into the vein and the one or more first temperature sensors are held in thermal contact with the skin by attachment to the skin attachment portion of the catheter anchoring device, the one or more first temperature sensors being adapted to detect a first temperature at a first skin temperature location;

one or more second temperature sensors for positioning on skin lateral and adjacent to the tip of the subcutaneously located IV catheter, and the one or more second temperature sensors are held in thermal contact with the skin by attachment to the skin attachment portion of the catheter anchoring device, the one or more second temperature sensors being adapted to detect a second temperature at a second skin temperature location;

an electronic thermometer operably connected to the one or more first and one or more second temperature sensors, the electronic thermometer being adapted to compare a temperature difference between the first temperature and the second temperature over time; and an alarm that is configured to be activated if the temperature difference between the first and second temperatures changes more than a predetermined amount over time; and wherein the skin attachment portion holds the one or more first and the one or more second temperature sensors at predetermined locations on the catheter anchoring device relative to the catheter capture portion such that the one or more first temperature sensors are positioned lateral and adjacent to the entry point of the IV catheter into the vein and the one or more second temperature sensors are positioned lateral and adjacent to the tip of the subcutaneously located IV catheter.

19. The fluid extravasation detection device of claim 18, wherein the one or more first and one or more second temperature sensors are thermistors.

20. The fluid extravasation detection device of claim 18, wherein the one or more first and one or more second temperature sensors are thermocouples.

21. The fluid extravasation detection device of claim 18, wherein the skin attachment portion holds the one or more first temperature sensors within areas defined by one or two semicircles centered on the entry point of the IV catheter into the vein with 3 cm radii, the one or two semicircles each having a straight side oriented parallel to and at least 0.5 cm lateral to the subcutaneously located IV catheter.

22. The fluid extravasation detection device of claim 18, wherein the skin attachment portion holds the one or more second temperature sensors within areas defined by one or two semicircles centered adjacent the tip of the catheter with 3 cm radii, the one or two semicircles each having a straight side oriented parallel to and at least 0.5 cm lateral to the subcutaneously located IV catheter.

23. The fluid extravasation detection device of claim 18, wherein the alarm is activated if the temperature difference between the first and second temperatures changes more than 0.1-2.0° C. over time.

24. The fluid extravasation detection device of claim 18, wherein the skin attachment portion includes a layer of thermally insulating foam material positioned over the one or more first and one or more second temperature sensors to insulate the first and second temperature sensors from environmental temperature influences.

25. The fluid extravasation detection device of claim 18, wherein all of the first and second temperature sensors are configured to be positioned adjacent to, and laterally spaced from, the vein.

* * * * *